US009126054B2

(12) United States Patent
Colborn

(10) Patent No.: US 9,126,054 B2
(45) Date of Patent: Sep. 8, 2015

(54) DEVICE LONGEVITY PREDICTION FOR A DEVICE HAVING VARIABLE ENERGY CONSUMPTION

(71) Applicant: CYBERONICS, INC., Houston, TX (US)

(72) Inventor: John C. Colborn, League City, TX (US)

(73) Assignee: CYBERONICS, INC., Houston, TX (US)

(*) Notice: Subject to any disclaimer, the term of this patent is extended or adjusted under 35 U.S.C. 154(b) by 0 days.

(21) Appl. No.: 14/276,652

(22) Filed: May 13, 2014

(65) Prior Publication Data

US 2014/0249602 A1 Sep. 4, 2014

Related U.S. Application Data

(62) Division of application No. 13/086,667, filed on Apr. 14, 2011, now Pat. No. 8,761,884.

(51) Int. Cl.
*A61N 1/06* (2006.01)
*A61N 1/378* (2006.01)
*A61N 1/36* (2006.01)
*A61N 1/372* (2006.01)

(52) U.S. Cl.
CPC ............ *A61N 1/378* (2013.01); *A61N 1/36053* (2013.01); *A61N 1/36064* (2013.01); *A61N 1/36114* (2013.01); *A61N 1/36135* (2013.01); *A61N 1/36139* (2013.01); *A61N 1/36146* (2013.01); *A61N 1/37235* (2013.01); *A61N 1/37247* (2013.01); *A61N 1/37264* (2013.01)

(58) Field of Classification Search
None
See application file for complete search history.

(56) References Cited

U.S. PATENT DOCUMENTS

| 3,796,221 A | 3/1974 | Hagfors |
| 4,324,251 A | 4/1982 | Mann |
| 4,488,555 A | 12/1984 | Imran |
| 4,556,061 A | 12/1985 | Barreras et al. |
| 4,686,990 A | 8/1987 | Moberg |

(Continued)

FOREIGN PATENT DOCUMENTS

| WO | 2001008749 | 2/2001 |
| WO | 2004075982 | 9/2004 |

OTHER PUBLICATIONS

Terry, R.S., et al., "The Implantable Neurocybernetic Prosthesis System," Pacing and Clinical Electrophysiology, vol. 14, No. 1, (Jan. 1991), pp. 86-93.

(Continued)

*Primary Examiner* — Brian T Gedeon
*Assistant Examiner* — Ankit Tejani
(74) *Attorney, Agent, or Firm* — Cyberonics, Inc.

(57) ABSTRACT

A system and method for estimating the longevity of an implantable medical device (IMD). In one embodiment of a method for estimating a life of a power source of an implantable medical device, a first life estimate of the power source is determined based on a first open-loop value corresponding to an open-loop parameter for open-loop therapy delivery, a first closed loop value corresponding to a closed-loop parameter for closed-loop therapy delivery, and prior usage data corresponding to prior therapy delivery. The first life estimate of the power source is displayed. The first life estimate displayed includes a first open-loop portion associated with open-loop therapy delivery and a first closed-loop portion associated with closed-loop therapy delivery.

18 Claims, 7 Drawing Sheets

(56) References Cited

U.S. PATENT DOCUMENTS

| | | | |
|---|---|---|---|
| 4,702,254 A | 10/1987 | Zabara |
| 4,715,381 A | 12/1987 | Moberg |
| 4,850,356 A | 7/1989 | Heath |
| 4,867,164 A | 9/1989 | Zabara |
| 4,899,750 A | 2/1990 | Ekwall |
| 4,964,407 A | 10/1990 | Baker et al. |
| 5,025,807 A | 6/1991 | Zabara |
| 5,127,404 A | 7/1992 | Wyborny et al. |
| 5,137,020 A | 8/1992 | Wayne et al. |
| 5,137,021 A | 8/1992 | Wayne et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,188,104 A | 2/1993 | Wernicke et al. |
| 5,193,538 A | 3/1993 | Ekwall |
| 5,201,808 A | 4/1993 | Steinhaus et al. |
| 5,201,865 A | 4/1993 | Kuehn |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,515 A | 7/1994 | Rutecki et al. |
| 5,335,657 A | 8/1994 | Terry, Jr. et al. |
| 5,344,431 A | 9/1994 | Merritt et al. |
| 5,352,962 A | 10/1994 | Galburt |
| 5,352,968 A | 10/1994 | Reni et al. |
| 5,372,607 A | 12/1994 | Stone et al. |
| 5,391,193 A | 2/1995 | Thompson |
| 5,431,692 A | 7/1995 | Hansen et al. |
| 5,458,624 A | 10/1995 | Renirie et al. |
| 5,496,353 A | 3/1996 | Grandjean et al. |
| 5,507,786 A | 4/1996 | Morgan et al. |
| 5,522,865 A | 6/1996 | Schulman et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,620,474 A | 4/1997 | Koopman |
| 5,703,469 A | 12/1997 | Kinoshita |
| 5,707,400 A | 1/1998 | Terry, Jr. et al. |
| 5,713,936 A | 2/1998 | Staub |
| 5,741,307 A | 4/1998 | Kroll |
| 5,741,311 A | 4/1998 | McVenes et al. |
| 5,755,742 A | 5/1998 | Schuelke et al. |
| 5,769,873 A | 6/1998 | Zadeh |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,925,068 A | 7/1999 | Kroll |
| 5,928,272 A | 7/1999 | Adkins et al. |
| 6,016,448 A | 1/2000 | Busacker et al. |
| 6,073,050 A | 6/2000 | Griffith |
| 6,108,579 A | 8/2000 | Snell et al. |
| 6,148,235 A | 11/2000 | Kuiper |
| 6,167,309 A | 12/2000 | Lyden |
| 6,181,969 B1 | 1/2001 | Gord |
| 6,185,461 B1 | 2/2001 | Er |
| 6,212,431 B1 | 4/2001 | Hahn et al. |
| 6,317,633 B1 | 11/2001 | Jorgenson et al. |
| 6,341,236 B1 | 1/2002 | Osorio et al. |
| 6,400,988 B1 | 6/2002 | Gurewitsch |
| 6,445,951 B1 | 9/2002 | Mouchawar |
| 6,453,198 B1 | 9/2002 | Torgerson et al. |
| 6,473,644 B1 | 10/2002 | Terry, Jr. et al. |
| 6,490,484 B2 | 12/2002 | Dooley et al. |
| 6,490,486 B1 | 12/2002 | Bradley |
| 6,553,263 B1 | 4/2003 | Meadows et al. |
| 6,587,719 B1 | 7/2003 | Barrett et al. |
| 6,587,727 B2 | 7/2003 | Osorio et al. |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,631,293 B2 | 10/2003 | Lyden |
| 6,648,823 B2 | 11/2003 | Thompson |
| 6,654,640 B2 | 11/2003 | Lyden |
| 6,658,294 B1 | 12/2003 | Zadeh et al. |
| 6,662,053 B2 | 12/2003 | Borkan |
| 6,671,552 B2 | 12/2003 | Merritt et al. |
| 6,671,556 B2 | 12/2003 | Osorio et al. |
| 6,687,538 B1 | 2/2004 | Hrdlicka et al. |
| 6,721,600 B2 | 4/2004 | Jorgenson et al. |
| 6,745,077 B1 | 6/2004 | Griffith et al. |
| 6,748,273 B1 | 6/2004 | Obel et al. |
| 6,760,624 B2 | 7/2004 | Anderson et al. |
| 6,760,625 B1 | 7/2004 | Kroll |
| 6,804,557 B1 | 10/2004 | Kroll |
| 6,820,019 B1 | 11/2004 | Kelly et al. |
| 6,901,293 B2 | 5/2005 | Rogers et al. |
| 6,940,255 B2 | 9/2005 | Loch |
| 7,142,923 B2 | 11/2006 | North et al. |
| 7,254,444 B2 | 8/2007 | Moore et al. |
| 7,751,891 B2 | 7/2010 | Armstrong et al. |
| 7,904,161 B2 | 3/2011 | Osypka |
| 2001/0034541 A1 | 10/2001 | Lyden |
| 2002/0022866 A1 | 2/2002 | Borkan |
| 2003/0074037 A1 | 4/2003 | Moore et al. |
| 2004/0039424 A1 | 2/2004 | Merritt et al. |
| 2004/0199146 A1 | 10/2004 | Rogers et al. |
| 2005/0088145 A1 | 4/2005 | Loch |
| 2005/0177206 A1 | 8/2005 | North et al. |
| 2005/0272280 A1 | 12/2005 | Osypka |
| 2007/0150019 A1 | 6/2007 | Youker et al. |
| 2007/0216366 A1 | 9/2007 | Inamine et al. |
| 2008/0097544 A1 | 4/2008 | Gandhi et al. |
| 2008/0177345 A1* | 7/2008 | Schmidt et al. ............ 607/29 |
| 2009/0099625 A1* | 4/2009 | Crowley et al. ............ 607/59 |
| 2010/0121591 A1 | 5/2010 | Hall |
| 2010/0145405 A1* | 6/2010 | Min et al. ............ 607/25 |
| 2010/0229187 A1* | 9/2010 | Marwah et al. ............ 719/318 |
| 2010/0274302 A1* | 10/2010 | Armstrong et al. ............ 607/2 |

OTHER PUBLICATIONS

Woodbury, J.W. et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

International Application No. PCT/US2007/000337, Written Opinion dated Jul. 27, 2008, 8 pgs.

International Application No. PCT/US2005/026514, Written Opinion dated Oct. 10, 2006, 4 pgs.

* cited by examiner

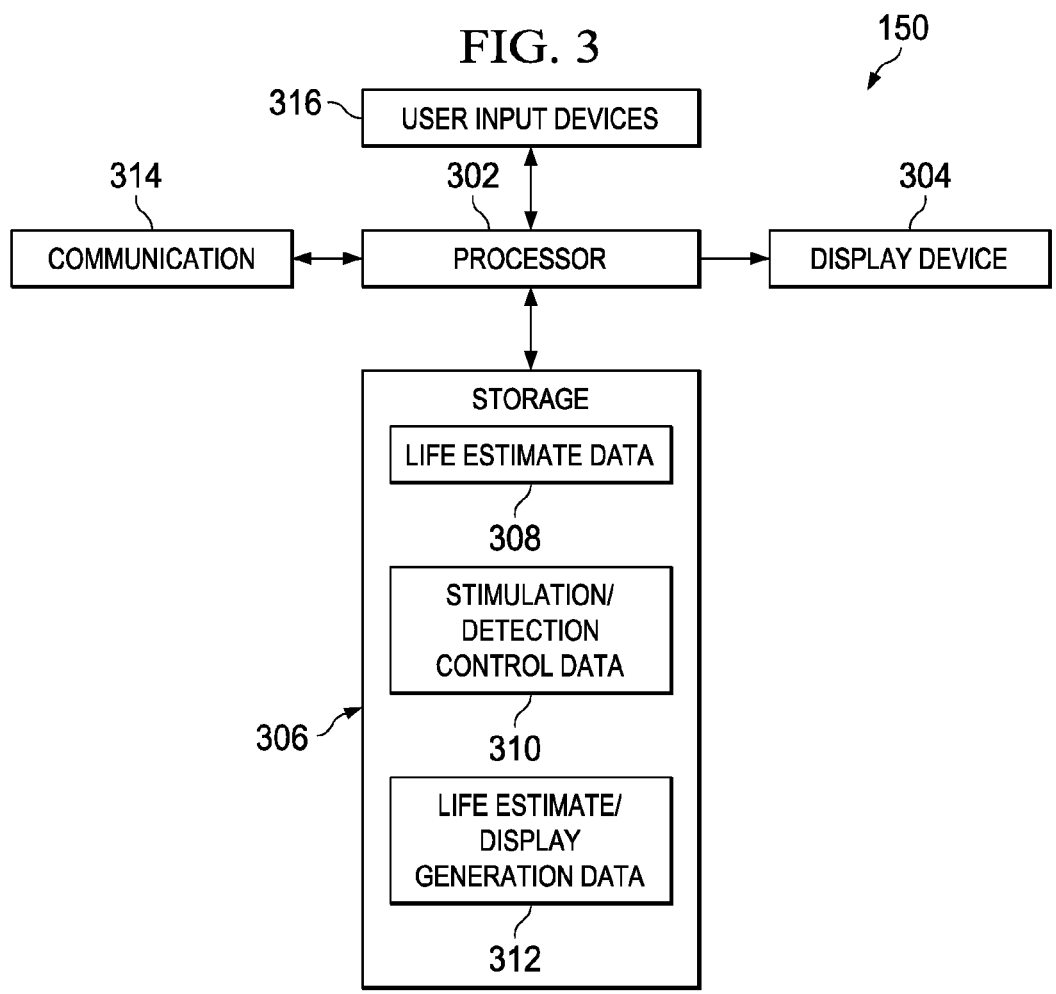

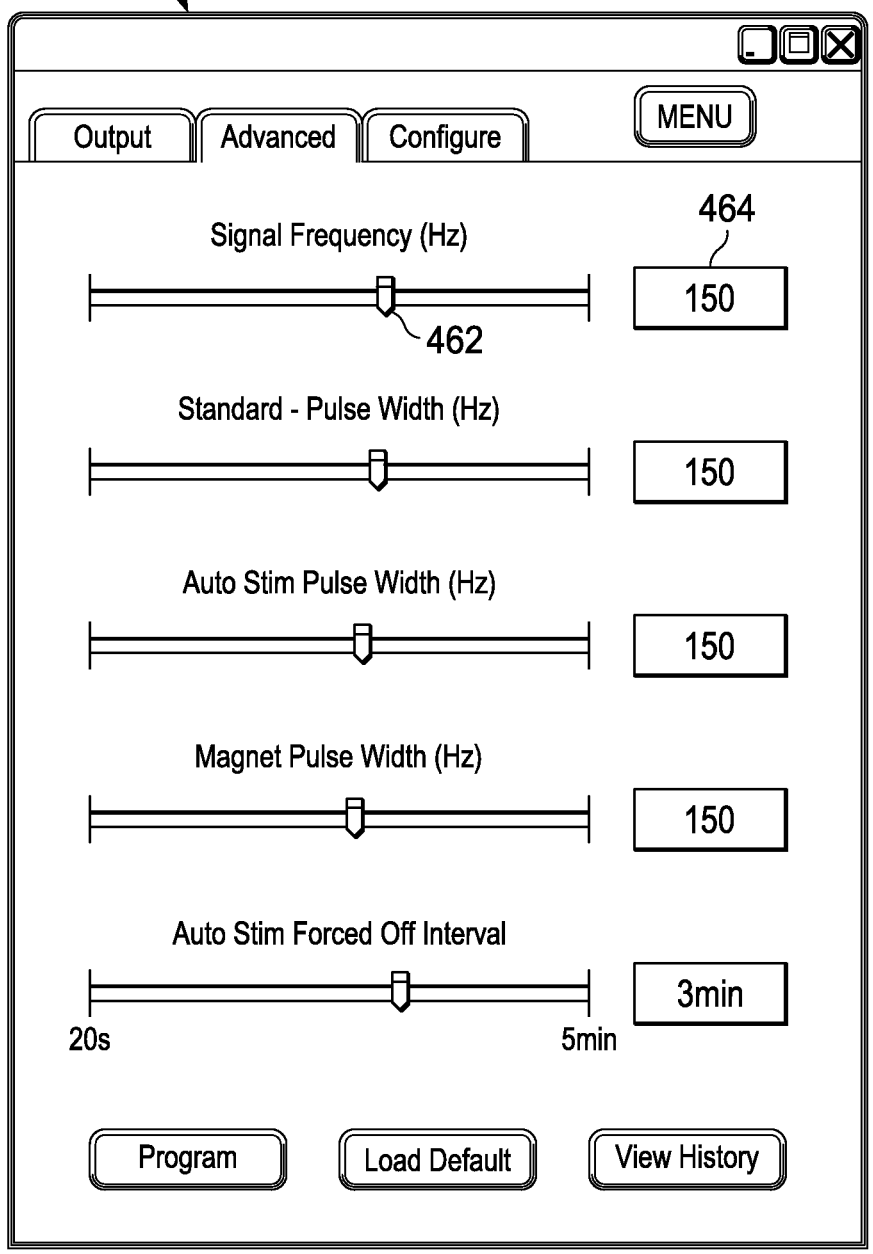

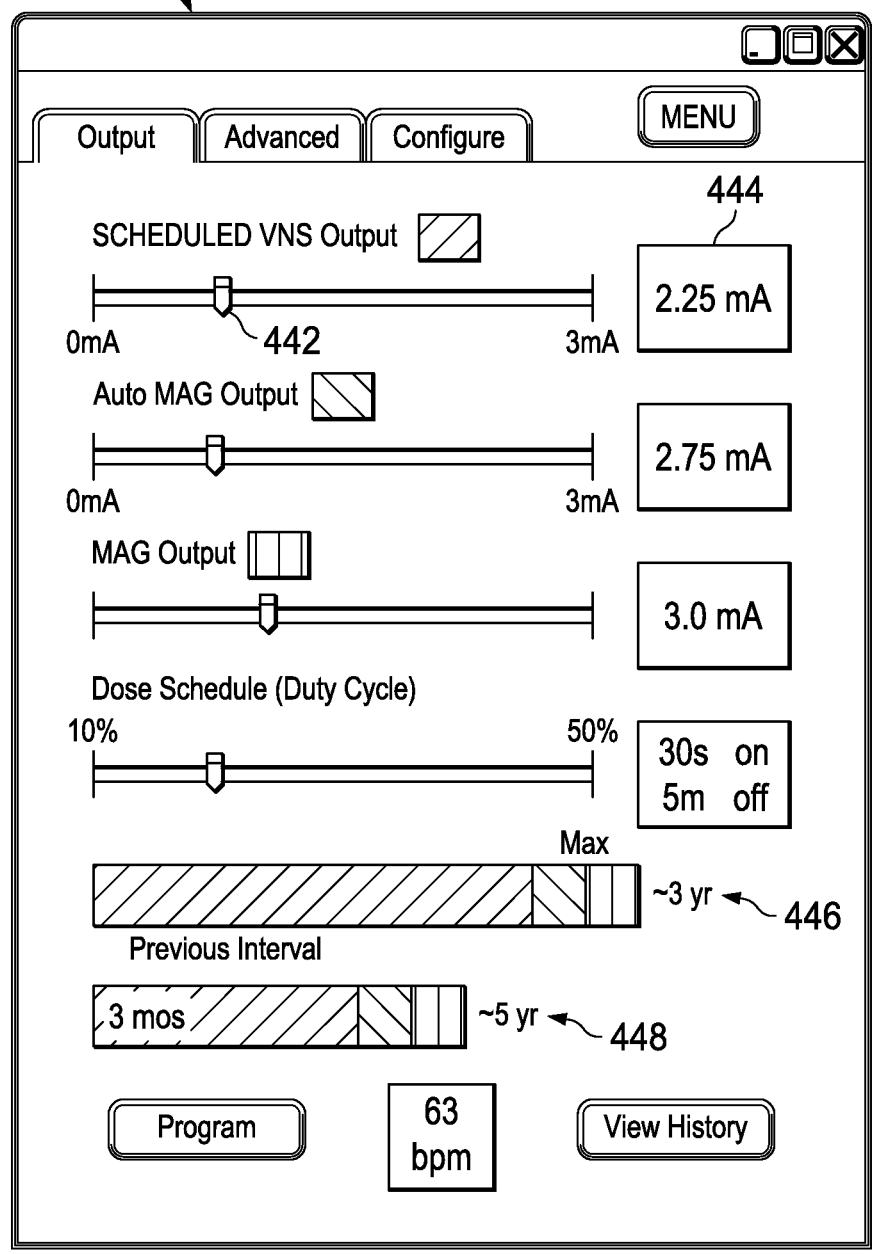

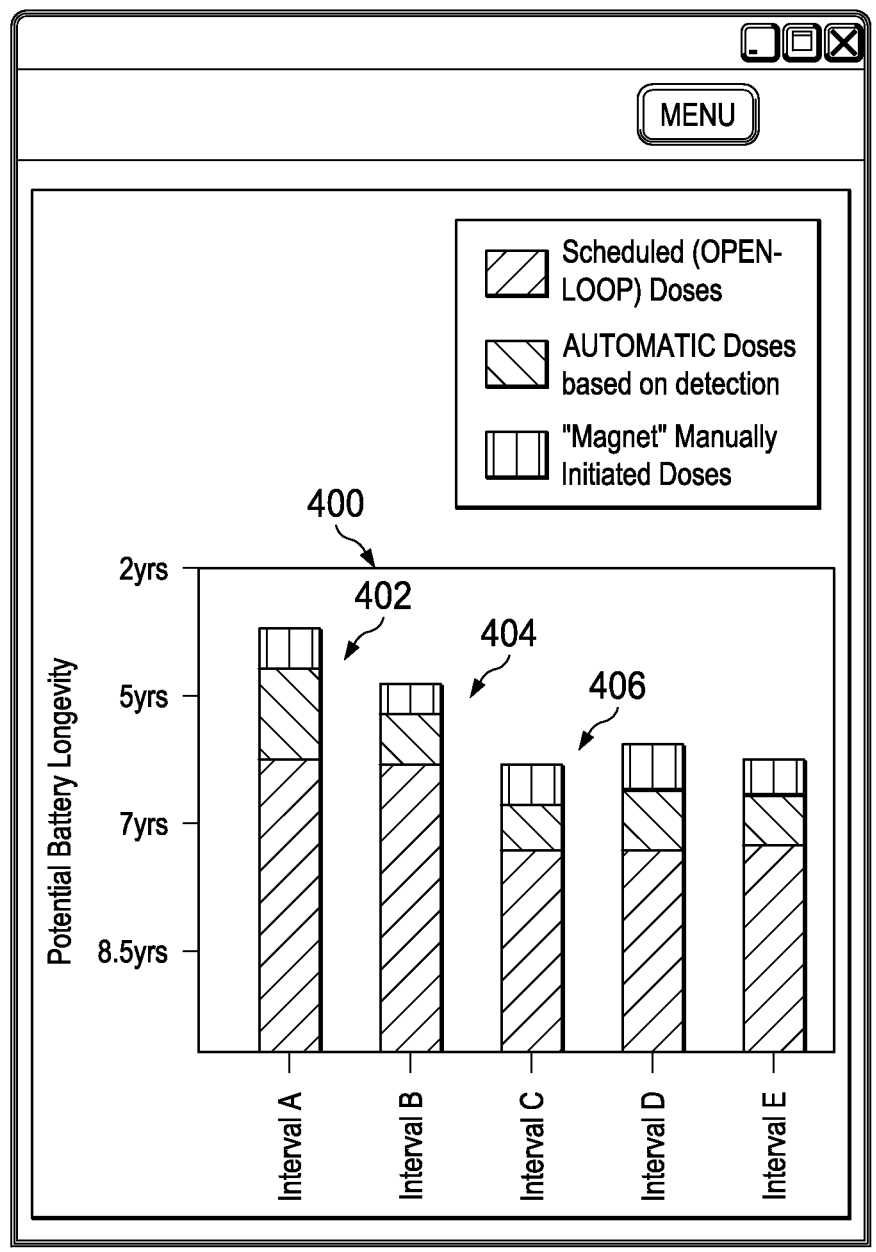

DEVICE LONGEVITY PREDICTION FOR A DEVICE HAVING VARIABLE ENERGY CONSUMPTION

CROSS-REFERENCE TO RELATED APPLICATION

This application is a divisional application of U.S. patent application Ser. No. 13/086,667, filed Apr. 14, 2011, now U.S. Pat. No. 8,761,884, and is hereby incorporated herein by reference in its entirety.

BACKGROUND

Medical treatments for disorders of the nervous system, such as seizure disorders (e.g., epilepsy), have improved in recent decades. One available treatment involves the application of an electrical signal to reduce various symptoms or effects caused by such neural disorders. For example, electrical signals have been successfully applied at strategic locations in the human body to provide various benefits, including a reduction of seizure occurrence and the improvement of other medical conditions. An example of such a treatment regimen involves the application of electrical stimulation to the vagus nerve of the human body to reduce or eliminate epileptic seizures, as described in U.S. Pat. No. 4,702,254, which is incorporated herein by reference.

Electrical stimulation of a target tissue of a patient's body may be provided by implanting an electrical device (known as an implantable medical device, or "IMD") underneath the skin of a patient and electrically stimulating the target tissue. In some cases, electrical stimulation of target tissue (including, but not limited to neural tissue such as the vagus nerve) may be delivered in accordance with a programmed (or predetermined or "planned") schedule. In such cases, the electrical stimulation is referred to as "open-loop," "passive," "programmed," or "non-feedback" stimulation. In other cases, electrical stimulation may be delivered in response to detecting some type of event. In one embodiment, the event may be patient-initiated, i.e., the patient may manually initiate stimulation by performing an action that is detected as an event ("manually-initiated" or "manually-requested" stimulation). In another embodiment, a change in one or more body parameters (for example, cardiac rhythm, muscle activity, or body movements) may be detected as an event that triggers electrical stimulation. Typically, the body parameter(s) is selected such that the change in the parameter is indicative of a disease state such as an epileptic seizure. Stimulation initiated based on a detected change in a body parameter is referred to as "automatic" or "automatically-initiated" stimulation. Event based stimulation, which includes manually initiated and/or automatic stimulation, is known as "closed-loop," "active" or "feedback" stimulation. In some devices, both open-loop and closed-loop stimulation may be simultaneously employed, with an open-loop program operating to provide a basic level of therapy and closed-loop stimulation provided in response to episodic events.

Whether delivered as closed-loop or open-loop, the stimulation is typically applied as a sequence of pulses (collectively referred to as a "burst") extending for a defined duration (known as the "on-time" or "burst duration"). In open-loop stimulation, the pulse bursts are separated by a programmed time period (the "off-time"), and in closed-loop stimulation the bursts are delivered in response to the detected event and may include a refractory period after the closed-loop burst to allow the nerve to recover. During the on-time of a pulse burst, electrical pulses of a defined electrical current (e.g., 0.5-3.5 milliamps) and pulse width (e.g., 0.25-1.0 milliseconds) are delivered at a defined frequency (e.g., 20-30 Hz) for the burst duration (e.g., 7-60 seconds). For open-loop stimulation, the on-time and off-time parameters together define a duty cycle, which is the ratio of the on-time to the combination of the on-time and off-time, and which describes the percentage of time that the electrical signal is applied to the nerve.

Most IMDs are powered by onboard batteries; consequently, the amount of power available is finite. Just before the battery of an IMD is exhausted, the IMD must be surgically removed from a patient's body so that a new device (or battery) may be installed. For this reason, the ability to accurately predict a battery's remaining life is crucial to ensuring that therapy to the patient is not interrupted, and to avoid endangering the patient's health. Overestimating an IMD's battery life can result in the undesirable interruption of therapy caused by not replacing the IMD and/or battery prior to exhaustion of its electrical charge. On the other hand, underestimating an IMD's battery life can result in surgery that is not then necessary, and a waste of the useful life of the IMD.

Predicting battery life generally is relatively uncomplicated when an IMD only applies electrical pulses in accordance with a planned schedule ("open-loop" stimulation). When closed-loop stimulation is used (either alone or in combination with open-loop stimulation), predicting battery life becomes difficult, because closed-loop stimulation is patient-specific and does not occur according to any predetermined schedule.

Thus, methods and systems for accurately predicting battery life in IMDs that apply closed-loop stimulation are desired.

SUMMARY

A system and method for estimating the longevity of an implantable medical device (IMD). In one embodiment, a method for estimating a life of a power source of an implantable medical device includes determining a first life estimate of the power source based on a first open-loop value corresponding to an open-loop parameter for open-loop therapy delivery, a first closed loop value corresponding to a closed-loop parameter for closed-loop therapy delivery, and prior usage data corresponding to prior therapy delivery. The first life estimate of the power source is displayed. The first life estimate displayed includes a first open-loop portion associated with open-loop therapy delivery and a first closed-loop portion associated with closed-loop therapy delivery.

In another embodiment, a system for estimating a life of a power source of an IMD includes therapy logic, detection logic, and a control device. The therapy logic is configured to provide open-loop therapy and closed-loop therapy to the patient. The detection logic is coupled to the therapy logic. The detection logic includes an algorithm configured to detect an event for triggering closed-loop therapy, and to record detected events. The control device is coupled to the therapy logic and the detection logic. The control device is configured to provide a first operable life estimate of the power source of the IMD. The first operable life estimate identifies a first open-loop therapy portion of the first life estimate and a first closed-loop therapy portion of the first life estimate.

In yet another embodiment, a method includes determining a first operable life estimate of an IMD. The first operable life estimate is based on a first operable life reduction attributable to a number of detected events operative to trigger closed-loop therapy and a second operable life reduction attributable to open-loop therapy. For the first operable life estimate, a first open-loop therapy portion associated with the second operable life reduction and a first closed-loop therapy portion associated with the first operable life reduction are identified.

In a further embodiment, an apparatus for controlling an IMD having a power source includes a processor and a display device. The processor is operative to generate an operable life estimate for the power source based on a number of open-loop therapies delivered during a first time period, a number of closed-loop therapy detection events during the first time period, a charge consumption associated with each open-loop therapy delivery; and a charge consumption associated with each closed-loop therapy delivery. The operable life estimate includes an open-loop therapy portion corresponding to operable life of the IMD used for open-loop therapy delivery and a closed-loop therapy portion corresponding to the operable life of the IMD used for closed-loop therapy delivery. The display device is coupled to the processor. The display device is operative to display the operable life estimate generated by the processor including the open-loop therapy portion and the closed-loop therapy portion.

BRIEF DESCRIPTION OF THE DRAWINGS

For a detailed description of exemplary embodiments of the present disclosure, reference will now be made to the accompanying drawings in which:

FIG. 3 shows a block diagram of the control unit, as shown in FIG. 1, in accordance with various embodiments;

FIGS. 4A-4D shows exemplary graphical displays provided by the control unit, as shown in FIG. 1, in accordance with various embodiments.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections. Further, the term "software" includes any executable code capable of running on a processor, regardless of the media used to store the software. Thus, code stored in memory (e.g., non-volatile memory), and sometimes referred to as "embedded firmware," is included within the definition of software.

DETAILED DESCRIPTION

The following discussion is directed to various embodiments of the present disclosure. The embodiments disclosed should not be interpreted, or otherwise construed, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

While accurately predicting battery life in an implantable medical device (IMD) that delivers both open-loop and closed-loop therapy may be difficult, reliable longevity information is important for use in tuning IMD operation to achieve a target IMD operational life, and for scheduling IMD replacement. Embodiments of the present disclosure provide device longevity estimates in a graphical form that highlights the effects of open-loop and closed-loop therapy on IMD operational life. Embodiments are configured to gather closed-loop operational information from an implanted IMD and model the effects of closed-loop therapy on IMD life. Embodiments also allow investigation of the effects of closed-loop therapy with no corresponding reduction in operable IMD life. Various embodiments are now described in detail with reference to the figures.

Figure 1:
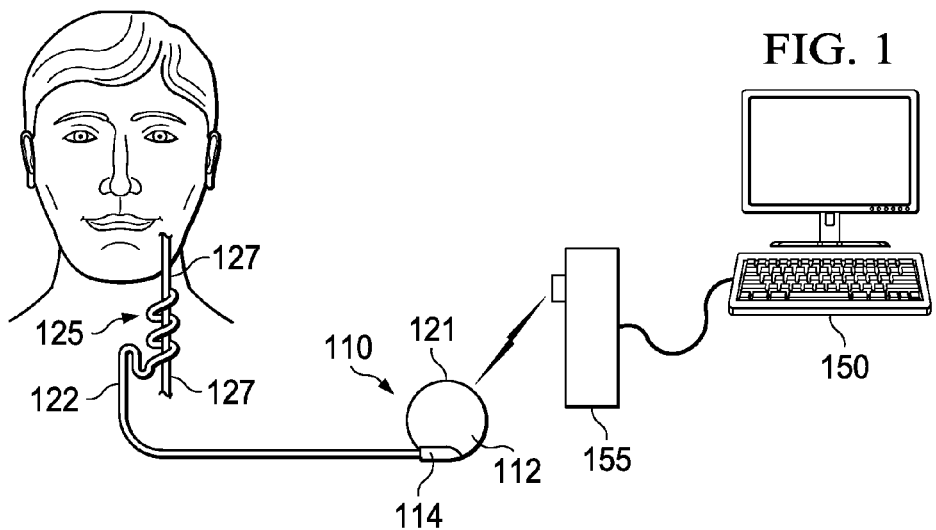
FIG. 1 shows an illustrative stimulation system coupled to a human cranial nerve in accordance with various embodiments.

FIG. 1 illustrates an implantable medical device 110 having a main body 112 comprising an enclosure or can 121 with a connector 114 (also referred to as the header) for connecting to leads 122. The IMD 110 is implanted in a patient's chest in a pocket or cavity formed by the implanting surgeon just below the skin, similar to the implantation procedure for a pacemaker pulse generator. A stimulating nerve electrode assembly 125, preferably comprising an electrode pair, conductively couples to the distal end of an insulated and electrically conductive lead assembly 122, which preferably comprises a pair of lead wires (one wire for each electrode of an electrode pair). Lead assembly 122 is attached at its proximal end to the connector 114 on can 121. The electrode assembly 125 is surgically coupled to a cranial nerve, such as a vagus nerve 127 in the patient's neck. The electrode assembly 125 preferably comprises a bipolar stimulating electrode pair, such as the electrode pair described in U.S. Pat. No. 4,573,481, which is incorporated herein by reference. Persons of skill in the art will appreciate that many electrode designs could be used in embodiments of the present disclosure. The two electrodes are preferably wrapped around the vagus nerve, and the electrode assembly 125 preferably is secured to the nerve 127 by a spiral anchoring tether such as that disclosed in U.S. Pat. No. 4,979,511, which is incorporated herein by reference. Lead assembly 122 may be secured, while retaining the ability to flex with movement of the chest and neck, by a suture connection to nearby tissue.

The IMD 110 may be controlled or programmed with a control unit 150 (e.g., a computer including any type of stationary, mobile, or handheld computing device) and a programming wand 155 to facilitate wireless communication between the control unit 150 and the IMD 110. The programming wand 155 permits noninvasive communication with the IMD 110 after the latter is implanted. In systems where the control unit 150 uses one or more channels in the Medical Implant Communications Service (MICS) bandwidths, the programming wand 155 may be omitted to permit more convenient communication directly between the control unit 150 and the IMD 110.

In at least some embodiments of the present disclosure, an estimate of longevity of a power source powering the IMD 110 is first made with the IMD 110 programmed to deliver only open-loop therapy, and to record when closed-loop therapy would have been delivered had closed-loop therapy been enabled. The recorded data may be provided to the control unit 150 in real-time or may be stored in IMD 110 for subsequent transfer to the control unit 150. The recorded data can then be used to estimate power source longevity. The estimation may be used to adjust IMD 110 parameters in consideration of estimated power source longevity and, if desired, closed-loop stimulation may thereafter be enabled. Furthermore, the estimation may be used to adjust IMD 110 parameters in consideration of estimated power source longevity in both the presence and absence of closed-loop therapy.

Alternatively, an initial longevity estimate is based on both an open-loop therapy program and predicted closed-loop therapy (based on the patient's personal medical condition history, event detector performance capabilities, and/or one or more of a variety of other factors). The initial longevity estimate may occur using the IMD 110 and the control unit 150, or it may occur in a surrogate environment, such as a computer based simulation. Subsequently, the rate of closed-loop therapy that is actually provided by the IMD 110 while the IMD 110 is implanted and operating inside the patient's body (i.e., the rate of closed-loop therapy "in real life") is recorded within the IMD 110 and later provided to the control unit 150 and used to adjust the estimate of power source longevity. Alternatively, the log may be provided in real-time to the control unit 150. In either case, the actual closed-loop therapy data is used to refine the initial estimate regarding longevity of the IMD 110.

Initial estimates and refinements thereto preferably are performed by the control unit 150 but also may be performed by the IMD 110. In some cases, portions of the initial estimates and/or refinements may be performed by the IMD 110 with the remainder of the estimates and/or refinements performed by the control unit 150. Both the initial estimates and refined predictions are displayed or otherwise provided to an end-user of the control unit 150 (e.g., the patient's physician). The end-user, such as the physician or patient, may adjust IMD 110 closed-loop algorithm parameters (e.g., event detection thresholds, stimulation current, etc.) in light of the estimated longevity and/or efficacy of the current therapy. The end-user also may enable or disable responsive, closed-loop therapy by the IMD 110. Further, the end-user may adjust the open-loop parameters (e.g., frequency, amplitude, pulse width) or disable open-loop therapy based on the performance and prediction information provided about all modes of therapy.

The IMD 110 illustrated in FIG. 1 provides electrical stimulation to a cranial nerve, such as the vagus nerve. However, the embodiments of the present disclosure are not limited to implantable devices that deliver electrical stimulation to a cranial nerve. Therapy may be delivered to any nerve, tissue, structure, or system of the body. Furthermore, the embodiments of the present disclosure are not limited to implantable devices that deliver electrical stimulation as a therapy. Any other type of therapy delivered by an implantable device may be used, such as a drug/chemical dosage delivery therapy, mechanical therapy (e.g., vibrations), optical, sound, or any other type of electromagnetic radiation therapy, or combination thereof.

Figure 2:
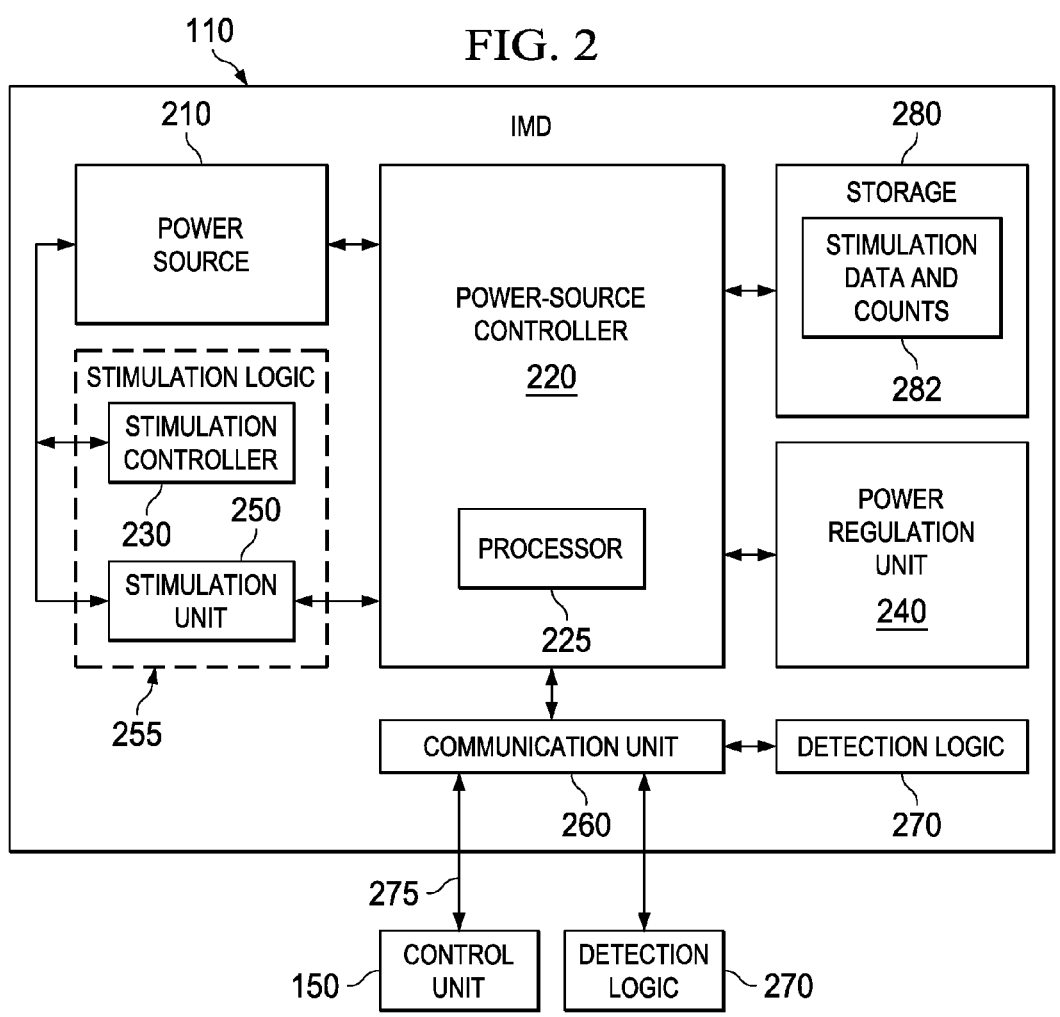
FIG. 2 shows a block diagram of the implantable medical device as shown in FIG. 1, in accordance with various embodiments.

FIG. 2 illustrates a block diagram of IMD 110 for performing neurostimulation in accordance with embodiments of the present disclosure. In one embodiment, the IMD 110 comprises a power source 210, a power-source controller 220, a stimulation controller 230, a power regulation unit 240, a stimulation unit 250, a communication unit 260, and storage 280. The stimulation controller 230 and stimulation unit 250 together form stimulation logic 255.

Storage 280 may be used for storing various program codes, starting data, and the like. More specifically, the storage 280 stores the parameter values that govern the rate and level of stimulation provided by the stimulation logic 255. The stored parameter values also enable delivery and/or logging of stimulation administered or events detected based on the different categories of stimulation (e.g., open-loop, automatically-initiated, manually-initiated). Information regarding the stimulation administered and/or stimulation trigger events detected is stored as stimulation data and counts 282 in the storage 280. The stimulation data and counts 282 may comprise a count of open-loop stimulations administered, a count of automatic stimulation trigger events detected, a count of automatic stimulation events administered, a count of received manually-initiated stimulation requests, and a count of manually-initiated stimulations delivered. The stored count values may be provided to the control unit 150 to facilitate prediction of the operational life of the IMD 110.

The power source 210 may comprise a battery, which may be rechargeable or non-rechargeable. Other power sources, such as capacitors, may also be used. The power source 210 provides power for the operation of the IMD 110, including electronic operations and stimulation bursts. Power source 210, in one embodiment, may be a lithium-thionyl chloride cell or a lithium/carbon monofluoride (LiCFx) cell. The terminals of the power source 210 preferably electrically couple to an input side of the power-source controller 220 and the power regulation unit 240. The power source 210 may be any type of rechargeable/replenishable source, or any type of non-rechargeable/non-replenishable source operative to provide power to the IMD 110.

The power-source controller 220 preferably comprises circuitry for controlling and monitoring the flow of electrical power to various electronic and stimulation-delivery portions of the IMD 110 (such as the components 230, 240, 250, 260 and 280 illustrated in FIG. 2). More particularly, the power-source controller 220 is capable of monitoring the power consumption or charge depletion of the IMD 110, measuring the voltage across the power source 210, and generating elective replacement and/or end-of-service signals.

The communication unit 260 facilitates communication between the IMD 110 and the control unit 150, as shown. The control unit 150 may be a device that is capable of programming various components and stimulation parameters of the IMD 110. In one embodiment, the control unit 150 is a computer system capable of electronic communications, programming, and executing a data-acquisition program. The control unit 150 may be controlled by a healthcare provider such as a physician in, for example, a doctor's office, or may be controlled by the patient. The control unit 150 may be used to download various parameters and program software into the IMD 110 for programming the operation of the IMD. The control unit 150 may also receive and upload various status conditions and other data from the IMD 110. The communication unit 260 may comprise hardware, software executed by a processor, or any combination thereof. Communications between the control unit 150 and the communication unit 260 may occur via a wireless or other type of communication, illustrated generally by line 275 in FIG. 2.

The power regulation unit 240 is capable of regulating power delivered by the power source 210 to particular components of the IMD 110 according to their needs and functions. The power regulation unit 240 may perform a voltage conversion to provide appropriate voltages and/or currents for the operation of the components. The power regulation unit 240 may comprise hardware, software executed by a processor, or any combination thereof. The communication unit 260 is capable of providing transmission and reception of electronic signals to and from a control unit 150.

Stimulation controller 230 defines the electrical stimulation pulses to be delivered as part of a burst to the nerve tissue according to parameters and waveforms that may be programmed into the IMD 110 using the control unit 150 or that may be pre-programmed into the controller 230 prior to or after implantation of the IMD 110 into the patient's body. The stimulation controller 230 controls the operation of the stimulation unit 250, which generates the stimulation pulses comprising a burst according to the parameters defined by the controller 230 and, in some embodiments, provides these pulses to the lead assembly 122 and electrode assembly 125. Stimulation pulses provided by the IMD 110 may vary widely across a range of parameters. The stimulation controller 230 may comprise hardware, software executed by a processor, or any combination thereof.

As previously explained, responsive, closed-loop bursts are delivered as a result of detecting some event. The detection logic 270 detects various events that may trigger delivery of a stimulation burst by the stimulation logic 255 (stimulation controller 230 and stimulation unit 250). For example, in some cases, the stimulation controller 230 and the stimulation unit 250 may deliver a stimulation burst in response to detection of an impending or already-occurring seizure based on one or more of the patient's cardiac parameters (e.g., heart rate, rate of change of heart rate, heart rate variability, etc.). However, detection logic 270 may be implemented anywhere on the patient's body to detect any type of event. For example, the detection logic 270 may be configured to detect events such as patterns of electrical activity in the brain, heart, or muscles, cardiac rhythms, blood pressure, respiratory patterns, etc. indicative of a condition treatable by the IMD. In some embodiments, the detection logic 270 may be disposed in a location other than the patient's body to detect some other type of event independent of the patient's body (e.g., a request for a stimulation burst initiated by the patient). Detection logic 270 may include a sensor (e.g., a sensor that detects a condition of the patient, or patient input, such as a tap or magnetic input apparatus). Further, the detection logic 270 may reside inside the IMD 110 and may be comprised of hardware, software executable by a processor, or any combination thereof. Upon detecting an event, the detection logic 270 causes the stimulation controller 230 to activate the stimulation unit 250 in response to the detected event. One or more of the blocks 210-280 may comprise hardware, software executed by a processor, or any combination thereof.

FIG. 3 shows a block diagram of the control unit 150, as shown in FIG. 1, in accordance with various embodiments of the invention. The control unit 150 includes a processor 302, storage 306, a display device 304, a communication unit 314, and user input devices 316. The control unit 150 may be implemented using any of various computing devices, such as desktop computer, a laptop/notebook computer, a tablet computer, a personal digital assistant (PDA), a smartphone, etc.

The processor 302 may a general purpose microprocessor, a digital signal processor, a microcontroller, or the like configured to execute instructions retrieved from a computer readable medium. In general, a processor may include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. Those skilled in the art understand that processors execute software instructions, and that software instructions alone are incapable of performing a function. Therefore, any reference to a function performed by software, or to software performing a function is simply a shorthand means for stating that the function is performed by a processor executing the software, or a processor executing the software performs the function.

The display device 304 may be a video display device, such as a liquid crystal display, a cathode ray display, a plasma display, an organic light emitting diode display, a vacuum fluorescent display, an electroluminescent display, an electronic paper display, a projection display, or other type of display or output device suitable for conveying information to a user. The display device 304 may be coupled to the processor 304 via a graphics adapter (not shown), or by other techniques known in the art. For example, the display device 304 may be remote from the processor 302 and data to be displayed may be transferred from the processor 302 to the display device 304 via a network.

The communication unit 314 may be configured to provide the control unit 150 with one or modes of communication. The communication unit 314 may provide wireless communication with the IMD 110 via one or more channels in the MICS. Communication with the programming wand 155 may be provided using any of a variety of wired signaling protocols (e.g., RS-232, RS-485, universal serial bus, etc) or any other wireless signaling protocols. The communication unit 314 may also allow the control unit 150 to connect to one or more wired or wireless networks, for example, a network in accordance with IEEE 802.11, IEEE 802.3, Ethernet, a cellular network, etc.

The user input device 316 allows a user (e.g., a physician) to control and/or provide information to the control unit 150. The user input device 316 may, for example, be any one or more of a keyboard, a mouse, a trackball, a touchpad, a touch screen, a keypad, buttons, a microphone and voice recognition system, a camera, a motion detection system, etc. The processor 302 may provide control information to the user input device 316, and Information input via the user input device 316 is transferred to and manipulated by the processor 302.

The storage 306 is a computer readable medium that may store instructions for execution by the processor 302, and other data for use by the processor 302. The storage 302 may include one or more types of non-volatile and/or volatile memory including: a hard disk, an optical disk, FLASH memory, read-only memory, random access memory, and/or other types of magnetic, optical, or semiconductor storage. The storage 306 may be external to the IMD 110 or may be the storage 280 of FIG. 2. Additionally, the execution of one or more of the instructions may be performed by the processor 225 of FIG. 2. The data stored in the storage 306 may be used by the processor 225 of FIG. 2.

The storage 306 stores life estimate/display generation data 312, stimulation/detection control data 310, and IMD life estimates data 308. The life estimate/display generation data 312 and the stimulation/detection control data 310 may include instructions that are executable by the processor 302. The life estimate/display generation data 312 includes instructions, that when executed by the processor 302, estimate the operable life of the IMD 110 (i.e., estimates the life of the power source 210), and generates displays of the operable life estimates for viewing on the display device 304. The operable life or longevity of the IMD 110 is the time period over which the power source 210 provides sufficient energy to guarantee proper operation of the IMD 110. The operable life estimates generated by the processor 302 using the life estimate/display generation data 312 are based on the capacity of the power source 210 consumed (e.g., charge consumed) by open-loop stimulation and closed-loop stimulation (automatic and manually-initiated). Because the rate of future closed-loop stimulations to be provided affects power source 210 life, but is difficult to accurately ascertain, some embodiments of the life estimate/display generation data 312 predict power source 210 life based on a measured rate of past closed-loop stimulation or past closed-loop stimulation trigger events recorded by the IMD 110 during an operating session (an interval of, for example, a period of weeks).

Some embodiments of the life estimate/display generation module 312 compute a power source life estimate (i.e., an estimate of the operable life of the IMD 110) based on the number of open-loop stimulations, automatic stimulations/stimulation requests, and manually-initiated stimulations/stimulation requests recorded by the IMD 110 in an operating session, in conjunction with the corresponding stimulation parameters (e.g., stimulation pulse width, current, frequency, etc.) applicable to each stimulation category (e.g., open-loop, automatic, manual). Operable life estimates provided by such embodiments may reflect the predicted life of the power source 210 based on the application of the measured rate of stimulation for each stimulation category using the corresponding stimulation parameters over the entire life of the power source 210. That is, an operable life estimate predicts what the life of the power source 210 would be if measured stimulation rates and corresponding stimulation parameters were applied over the full (i.e., from beginning to end) life of the IMD 110.

A life estimate display generated from the life estimate/display generation data 312 identifies what portions of the total estimated operable life of the IMD 110 are consumed by open-loop stimulations, automatic stimulations, and manually-initiated stimulations. By providing the operable life estimate display based on stimulation categories, the control unit 150 allows the user to adjust the stimulation/detection parameters to provide more or less detection sensitivity for automatic stimulation events, and more or less energy per stimulation for each stimulation category thereby tuning operation of the IMD 110 to achieve a desired operable IMD life. For example, if automatic stimulations are judged, based on a display of operable IMD life, to be consuming excessive IMD life, then the user may reduce the sensitivity of event detection that initiates automatic stimulation, thereby reducing the number of events detected, or the user may reduce the stimulation energy applied in response to a detected event.

Figure 4A:
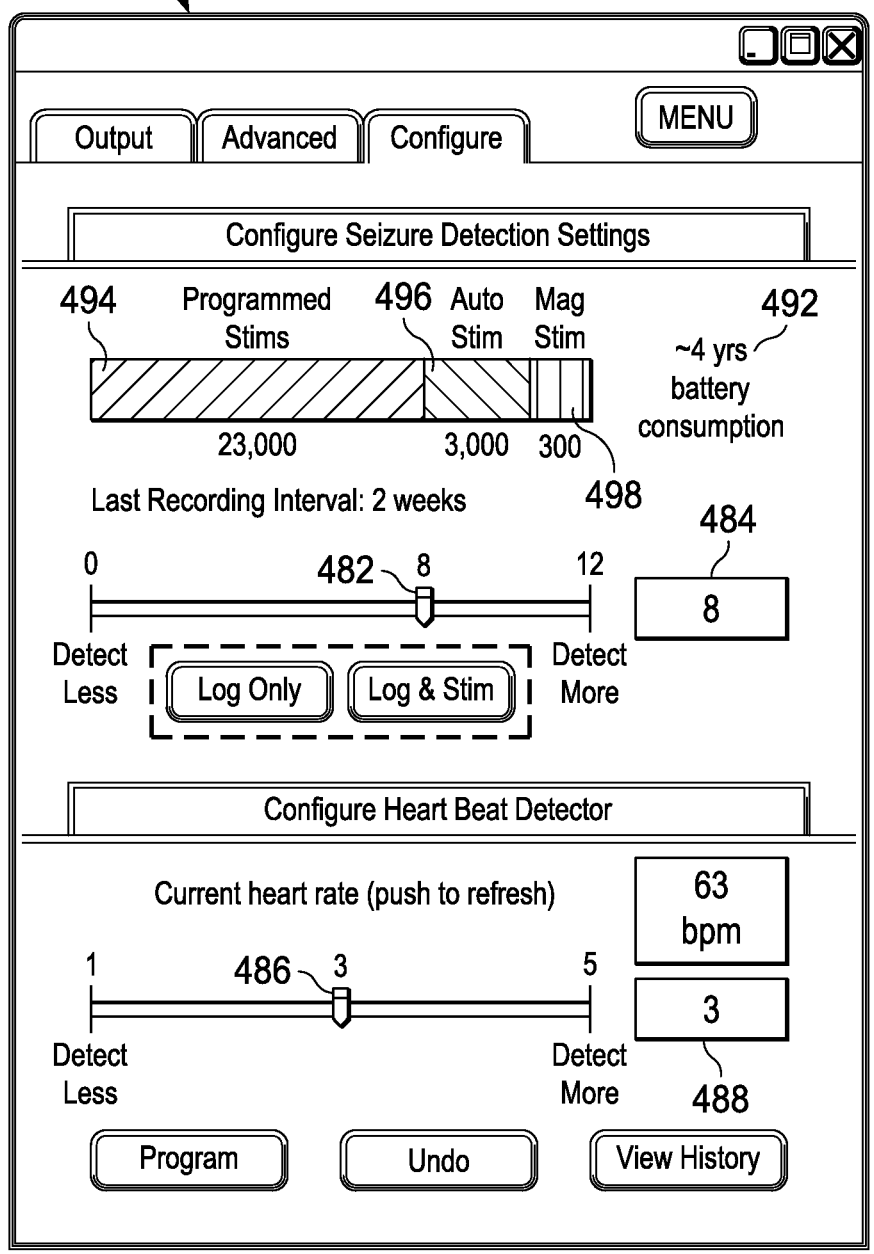

The stimulation/detection control module 310, when executed by the processor 302, allows the user to input information for controlling the sensitivity of event detection for automatic stimulation. FIG. 4A shows an exemplary display 480 included in a graphical user interface with control and input features provided by the stimulation/detection control software 310. A level of event detection sensitivity may entered by a user via a control feature, such as the sliders 482, 486, the text boxes 484, 488, etc.

The stimulation/detection control software 310 allows the user to control whether the IMD 110 provides stimulation in response to a detected event in addition to logging the detection of the event. Buttons 490 (e.g., radio buttons) provide the logging/stimulation selection. The capability to log detected events without providing automatic stimulation can be useful for determining the number of events detected at a particular sensitivity level without a corresponding reduction in IMD life.

The display 480 also includes a graphical display 492 of the estimated life of the IMD 110. The estimated life display 492 is broken down into segments 494, 496, and 498 showing a portion of total IMD life respectively consumed by open-loop, automatic, and manually-initiated stimulations. The estimated life display segment 496 corresponding to automatic stimulation is updated in response to changing the event detection sensitivity, thereby providing the user with feedback regarding the effect of a change in sensitivity on IMD life. An indication is made to the user (e.g., via the graphical display 492) to delineate actual counts (e.g., from previous recording intervals).

FIG. 4B shows an exemplary display 460, included in a graphical user interface generated by the stimulation/detection control module 310, for setting parameters (e.g., frequency, pulse width, etc.) related to open-loop, automatic, and manually-initiated stimulations. Each parameter is user adjustable using a control feature, such as the slider 462, the text box 464, etc. Changes to these parameters may affect the operable life of the IMD 110, and therefore may be reflected in an update of the graphical display of operable life provided to the user (e.g., display 492).

FIG. 4C shows an exemplary display 440, included in a graphical user interface generated by the stimulation/detection control module 310, for setting dose schedule and setting output current for open-loop, automatic, and manually-initiated stimulations. Each parameter is user adjustable using a control feature, such as the slider 442, the text box 444, etc. The display 440 also includes a graphical display 446 of the estimated life of the IMD 110 based on stimulation and detection parameters used by the IMD 110 during a previous use interval (e.g., the last use session). An additional graphical display 448 of estimated IMD life shows predicted IMD life based on the current setting applied to the stimulation and detection parameters. Thus, changes in the current and/or dose settings are reflected in the graphical display 448 for comparison with the display 446 of estimated life based on the previously used parameters and IMD recorded stimulation information. The estimated life displays 446, 448 are broken into segments showing a portion of total IMD life respectively consumed by open-loop, automatic, and manually-initiated stimulations.

A plurality of life estimates 308 may be recorded in the storage 282 and 306. Each stored life estimate corresponds to a log of stimulations and detected events recorded by the IMD 110 during an operating session, and the stimulation parameters applied during the operating session. One or more of the recorded life estimates may be displayed to provide a history of life estimates for the IMD 110. FIG. 4D shows a graphical display 400 of a plurality of life estimates 308. Each life estimate corresponds to a stored life estimate as described above, and shows a portion of IMD 110 operable life consumed by open-loop, automatic, and manually-initiated stimulations. For example, based on the use of the IMD 110 during the operating session of Interval A, which may be a period of weeks, the operable life of the IMD 110 is estimated to be less than 5 years. Any number of parameters, in addition to those provided in FIGS. 4A-D, may be provided to modify the different types of stimulation. For example, a physician may set a threshold that limits the number of manually-initiated stimulations within a period of time to limit battery consumption and health risks (e.g., side effects) from unnecessary stimulation.

Figure 5:
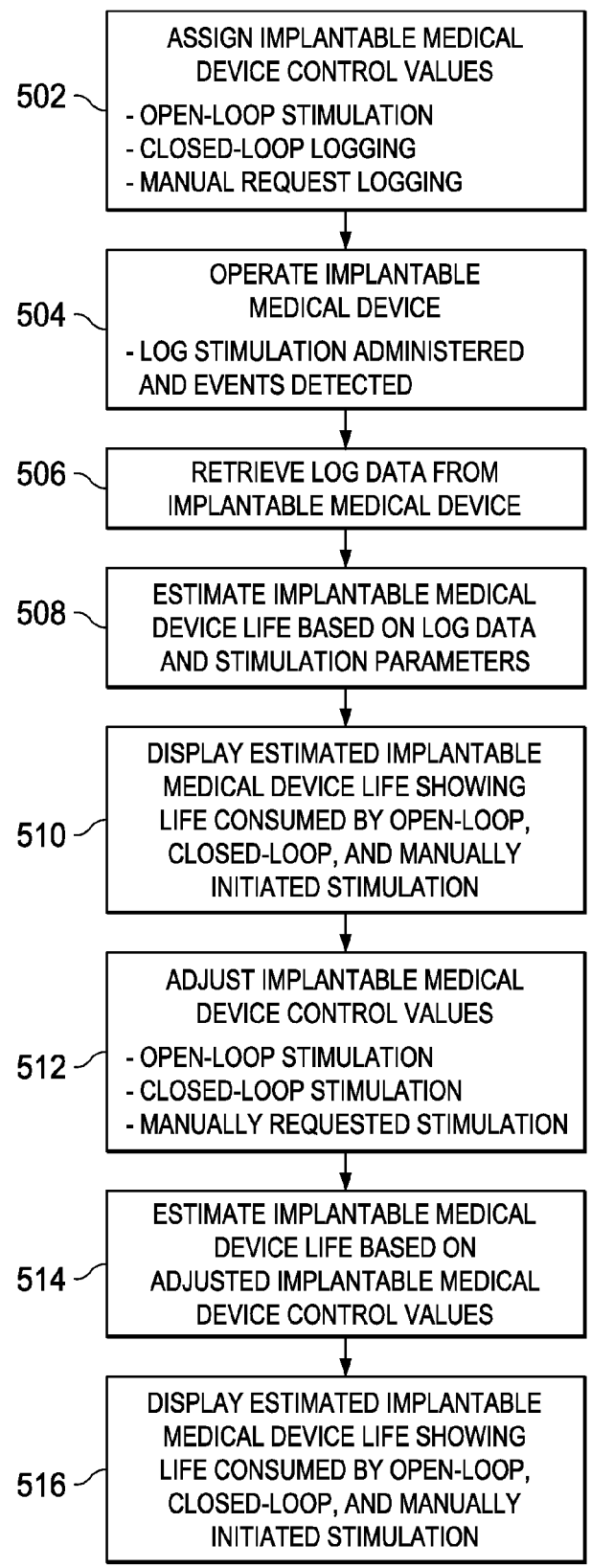
FIG. 5 shows a flow diagram of an illustrative method for predicting longevity of the implantable medical device, as shown in FIG. 1, in accordance with various embodiments.

FIG. 5 shows a flow diagram of an illustrative method for predicting longevity of the IMD 110 in accordance with various embodiments of the invention. Though depicted sequentially as a matter of convenience, at least some of the actions shown can be performed in a different order and/or performed in parallel. Additionally, some embodiments may perform only some of the actions shown. Embodiments of the method may be implemented by the IMD 110 and/or the control unit 150 as disclosed herein. In some embodiments, at least some of the operations of FIG. 5, as well as other operations described herein, can be implemented as instructions stored in a computer readable medium and executed by a processor.

In block 502, a user of the control unit 150 assigns a first set of values to IMD control parameters. The control parameters may include open-loop stimulation rate and level, automatic stimulation level, manually-initiated stimulation level, event detection level for automatic stimulation, and automatic and manually-initiated stimulation/logging enablement controls. The first set of values configures the IMD 110 to provide open-loop stimulation. The rate and level of open-loop stimulation may be selected to provide the IMD 110 with a desired longevity (e.g., 5-6 years). The first set of values may further configure the IMD 110 to disable automatic stimulation and manually-initiated stimulation, while enabling logging of detection of events that trigger automatic stimulation and logging of requests for manually-initiated stimulation. If disabled, automatic and manually-initiated stimulation do not contribute to depletion of the power source 210, but detected event logging allows for acquisition of potential stimulation information that can be used to estimate energy consumption had closed-loop stimulation been enabled.

In some embodiments, archived longevity data (e.g., generalized longevity information based on measured longevity of previously implanted IMDs using known open-loop and/or closed-loop stimulation parameters) may be applied to select the open-loop and closed-loop stimulation parameters and to estimate longevity of the IMD 110. The archived longevity data may be non-patient specific, and may be particularly useful in estimating IMD longevity before patient specific longevity information is acquired. However, embodiments may apply archived longevity data to estimating the longevity of the IMD 110, alone or in combination with patient specific longevity information, at any point in the life of the IMD 110.

In block 504, the IMD 110 is operated for a first interval (e.g., a session covering a period of weeks) as configured by the first set of values. The IMD 110 provides open-loop stimulation, and records the number of open-loop stimulations, the number of detected automatic stimulation events, and the number of requests for manually-initiated stimulation in a log 282 in the storage 280.

In block 506, at the completion of the operating session, the control unit 150 retrieves the stimulation and detected event information logged by the IMD 110 during the operating session. The control unit 150 may retrieve the logged information via the communication units 260, 314. Alternatively, the IMD 110 provides the information to the control unit 150 during the operating session.

In block 508, the control unit 150 estimates the operable life of the IMD 110 based on the retrieved stimulation and detected event information. The IMD life estimate is further based on the stimulation level parameters (e.g., stimulation current, pulse width, etc.) used by the IMD 110 during the operating session. The stimulation level parameters may be transferred from the IMD 110 to the control unit 150, or retrieved from control unit storage 306. In some embodiments, IMD life estimation includes determining the energy consumed by the stimulations administered, and stimulations that would have been administered had automatic or manually-initiated stimulation been enabled, and determining the life of power source 210 if the determined session energy consumption were applied over the entire life of the power source 210. The portion of total power source energy consumed by each category of stimulation may be determined based on the number of stimulations and the charge consumption or potential charge consumption per stimulation for the category during the operating session.

In block 510, the control unit 150 presents a display (e.g., display 400) of the estimated longevity of the IMD 110. The display shows the total estimated life of the IMD 110, and shows what portion of the total estimated life is consumed by each of open-loop stimulation, automatic stimulation, and manually-initiated stimulation based on the stimulation rate, stimulation level, and other stimulation parameters applied during the operating session. IMD life display 402 of FIG. 4D is an example of a display of an IMD life estimate wherein the IMD 110 is operated using open-loop stimulation configured to provide an estimated six year power source life, automatic and manually-initiated stimulation are disabled, and detected automatic stimulation events and requests for manually-initiated stimulation are logged.

In block 512, the IMD control values are adjusted based on the estimated IMD life. Open-loop stimulation rate and/or level may be adjusted to allow for the anticipated energy consumption of automatic and manually-initiated stimulation. Automatic stimulation event detection sensitivity may be adjusted based on the number and/or level of events detected in the previous operating session. Stimulation levels for automatic and/or manually-initiated stimulation may be adjusted to provide a desired longevity for the power source 210. Automatic and/or manually-initiated stimulation may be disabled to allow for further acquisition of detected event information without affecting the life of the power source 210, or automatic and/or manually-initiated stimulation may be enabled.

In block 514, the control unit 150 generates a new operable life estimate for the IMD 110 based on the adjusted IMD control values. A display representing the new estimate of IMD life is presented, by the control unit 150, in block 516. The display shows total estimated IMD life and portions of IMD life allocated to open-loop, automatic, and manually-initiated stimulation allowing the user to further adjust the stimulation parameters and receive immediate feedback as to the effects of the adjustments on IMD life.

IMD life display 404 of FIG. 4D is an example of a display of an IMD life estimate wherein the automatic stimulation level and/or detection sensitivity has been adjusted based on the detected number of automatic stimulation events (or IMD life potentially consumed by automatic stimulation events) of the prior operating session (as shown in display 402). The IMD 110 is operated for a second session (FIG. 4D, Interval B) using open-loop stimulation configured to provide an estimated six year power source life, automatic stimulation and manually-initiated stimulation are disabled, and detected closed-loop stimulation events are logged.

IMD life display 406 of FIG. 4D is an example of a display of an IMD life estimate wherein the open-loop stimulation rate and level has been adjusted to reduce the scheduled open-loop stimulation, but the automatic stimulation and manually-initiated stimulation remain unchanged. The IMD 110 is operated for a third session (Interval C) with open-loop stimulation, automatic stimulation, and manually-initiated stimulation enabled and configured to provide an estimated 6 year operational life for the IMD 110. Thus, the desired six year operational life is maintained over the various operating sessions while adjusting operating parameters applied to the different categories of stimulation.

The efficacy of the therapy may be considered when adjusting the therapy parameters to provide the most efficacious therapy using the least amount of power. The adjustments to the parameters and considerations of efficacy and battery life may be applied in an iterative fashion. In this manner, the needed level of therapy may be provided to the patient while maximizing the life of the IMD power source.

The above discussion is meant to be illustrative of various principles and embodiments of the present invention. Numerous variations and modifications will become apparent to those skilled in the art once the above disclosure is fully appreciated. For example, while embodiments have been described with reference to estimating power source longevity, those skilled in the art will understand that embodiments are also applicable to estimating the longevity of other depletable resources (e.g., a drug supply) of an IMD. It is intended that the following claims be interpreted to embrace all such variations and modifications.

What is claimed is:

1. A system for estimating a life of a power source of an implantable medical device (IMD), the system comprising:
a therapy logic configured to provide an open-loop stimulation therapy, an automatic closed-loop stimulation therapy, and a manually-initiated closed-loop stimulation therapy to a patient;
a detection logic coupled to the therapy logic, the detection logic configured to detect one or more events for triggering the automatic closed-loop stimulation therapy and the manually-initiated closed-loop stimulation therapy, and to record the one or more events; and
a control device coupled to the therapy logic and the detection logic, the control device configured to provide a first operable life estimate of the power source of the IMD, wherein the first operable life estimate identifies a first open-loop stimulation therapy portion of the first operable life estimate, a first automatic closed-loop stimulation therapy portion of the first operable life estimate, and a first manually-initiated closed-loop stimulation therapy portion, and where the first operable life estimate is based on an open-loop value corresponding to an open-loop parameter for the open-loop stimulation therapy, a closed-loop value corresponding to a closed-loop parameter for the automatic closed-loop stimulation therapy, a second closed-loop value corresponding to a manually-initiated closed-loop parameter for the manually-initiated closed-loop stimulation therapy, and a prior usage data corresponding to prior therapy delivery.

2. The system of claim 1, wherein the therapy logic is configured to enable a user to selectively enable and disable application of the automatic closed-loop stimulation therapy, the manually-initiated closed-loop stimulation therapy, and the open-loop stimulation therapy based in part on the first operable life estimate including the first open-loop therapy portion, the first automatic closed-loop stimulation therapy portion, and the first manually-initiated closed-loop stimulation therapy portion.

3. The system of claim 1, wherein the control device is configured to update the first operable life estimate based on changing a parameter value corresponding to at least one of the open-loop stimulation therapy, the automatic closed-loop stimulation therapy, and the manually-initiated closed-loop stimulation therapy.

4. The system of claim 1, wherein the control device is configured to retrieve control information from the IMD and to provide an estimation of an operable life of the power source based on the control information.

5. The system of claim 4, wherein the control information specifies a period and therapy level for the open-loop therapy, a first detection level and a first therapy level for the automatic closed-loop stimulation therapy, and a second detection level and a second therapy level for the manually-initiated closed-loop stimulation therapy.

6. The system of claim 1, wherein an estimation of an operable life of the power source represents an entire life of the power source.

7. The system of claim 1, wherein the control device is configured to store a plurality of operable life estimates, each estimate corresponding to a set of control information provided to a stimulation logic and the detection logic over a life of the power source, and to generate a display of the plurality of operable life estimates.

8. The system of claim 1, wherein the automatic closed-loop stimulation therapy and the manually-initiated closed-loop stimulation therapy to the patient are disabled, and wherein the first automatic closed-loop stimulation therapy portion is determined at least in part based on a count of automatic stimulation trigger events detected, and the first manually-initiated closed-loop stimulation therapy portion is determined at least in part on a count of manually-initiated stimulation requests detected.

9. A method, comprising:
determining a first operable life estimate of an implantable medical device (IMD), the first operable life estimate is based on a first operable life reduction attributable to a number of detected events operative to trigger an automatic closed-loop stimulation therapy, a second operable life reduction attributable to an open-loop stimulation therapy, and a third operable life reduction attributable to a manually-initiated closed-loop stimulation therapy;
identifying, for the first operable life estimate, a first open-loop stimulation therapy portion associated with the second operable life reduction, a first automatic closed-loop therapy portion associated with the first operable life reduction, and a first manually-initiated closed-loop stimulation therapy portion associated with the third operable life reduction.

10. The method of claim 9, further comprising:
displaying the first operable life estimate including the first open-loop stimulation therapy portion, the first automatic closed-loop stimulation therapy portion, and the first manually-initiated closed-loop stimulation therapy portion on an external device.

11. The method of claim 9, further comprising:
changing a value at the IMD, the value affecting any of an open-loop stimulation therapy level, an open-loop stimulation therapy rate, an automatic closed-loop detection level, and an automatic closed-loop therapy level, a manually-initiated closed-loop detection level, and a manually-initiated closed-loop therapy level;
determining a second operable life estimate of the IMD based on the changed value;
identifying, for the second operable life estimate, a second open-loop stimulation therapy portion, a second automatic closed-loop stimulation therapy portion, and a second manually-initiated closed-loop stimulation therapy portion based on the changed value; and
displaying the second operable life estimate including the second open-loop stimulation therapy portion, the second automatic closed-loop stimulation therapy portion, and the second manually-initiated closed-loop stimulation therapy portion on an external device.

12. The method of claim 11, further comprising:
displaying the first operable life estimate including the first open-loop stimulation therapy portion, the first automatic closed-loop stimulation therapy portion, and the first manually-initiated closed-loop stimulation therapy portion on the external device concurrently with the second operable life estimate including the second open-loop stimulation therapy portion, the second automatic closed-loop stimulation therapy portion, and the second manually-initiated closed-loop stimulation therapy portion.

13. The method of claim 12, wherein the first operable life estimate and the second operable life estimate are displayed prior to the IMD operating with the changed value.

14. The method of claim 9, further comprising:
storing a plurality of operable life estimates, each estimate corresponding to a different programming of the IMD over a life of the IMD; and
displaying the plurality of operable life estimates.

15. An apparatus for controlling an implantable medical device (IMD), the IMD having a power source, the apparatus comprising:
a processor operative to generate an operable life estimate for the power source based on a number of open-loop therapies delivered during a first time period, a number of closed-loop therapy detection events during the first time period, a charge consumption associated with each open-loop therapy delivery, and a charge consumption associated with each closed-loop therapy delivery, wherein the operable life estimate comprises an open-loop therapy portion corresponding to operable life of the IMD used for open-loop therapy delivery, an automatic closed-loop therapy portion corresponding to the operable life of the IMD used for automatic closed-loop therapy delivery, and a manually-initiated closed-loop therapy portion corresponding to an operable life of the IMD used for manually-initiated closed-loop therapy delivery; and
a display device coupled to the processor, the display device operative to display the operable life estimate generated by the processor including the open-loop therapy portion, the automatic closed-loop therapy portion, and the manually-initiated closed-loop therapy portion.

16. The apparatus of claim 15, wherein the processor is further operative to update the operable life estimate based on a change in one or more values affecting at least one of the open-loop therapy delivery, the automatic closed-loop therapy delivery, and the manually-initiated closed-loop therapy delivery.

17. The apparatus of claim 16, wherein the display device is operative to display an updated operable life estimate concurrently with the operable life estimate.

18. The apparatus of claim 17, wherein the updated operable life estimate and the operable life estimate are concurrently displayed prior to operation of the IMD with the changed one or more values.

* * * * *